United States Patent

Kunkel et al.

[11] Patent Number: 5,958,468
[45] Date of Patent: Sep. 28, 1999

[54] POLYMERIZATION APPARATUS

[75] Inventors: Peter Kunkel, Triesen, Liechtenstein; Jürgen Mertins, Gams, Switzerland; Eckart Walser, Vaduz, Liechtenstein

[73] Assignee: Iuoclar AG, Schaan, Liechtenstein

[21] Appl. No.: 08/851,949

[22] Filed: May 5, 1997

[30] Foreign Application Priority Data

May 8, 1996 [DE] Germany ............................ 196 18 543

[51] Int. Cl.⁶ ........................ A61C 13/14; B29C 51/28; B29C 51/42
[52] U.S. Cl. ........................ 425/174.4; 425/389
[58] Field of Search .............................. 425/174.4, 389; 264/425, 401, 463, 494; 250/492.1, 503.1, 494.1, 491.1

[56] References Cited

U.S. PATENT DOCUMENTS

| | | | |
|---|---|---|---|
| 3,682,571 | 8/1972 | Greenberg et al. | 425/174.4 |
| 4,395,211 | 7/1983 | Broeksema et al. | 425/174.4 |
| 4,421,987 | 12/1983 | Herold | 250/492.1 |
| 4,576,776 | 3/1986 | Anderson | 425/389 |
| 4,582,998 | 4/1986 | Gonser et al. | 250/492.1 |
| 5,037,599 | 8/1991 | Olson | 425/389 |
| 5,071,337 | 12/1991 | Heller et al. | 425/174.4 |
| 5,135,695 | 8/1992 | Marcus | 264/141 |
| 5,573,877 | 11/1996 | Inoue et al. | 430/30 |
| 5,726,919 | 3/1998 | Azad et al. | 364/578 |

FOREIGN PATENT DOCUMENTS

| | | |
|---|---|---|
| E 44 450 | 12/1984 | Austria. |
| 82 09 544.2 U1 | 2/1983 | Germany. |
| 3529800 A1 | 3/1986 | Germany. |
| 2101518 | 1/1983 | United Kingdom ............... 425/174.4 |
| 95/08300 A1 | 3/1995 | WIPO. |

*Primary Examiner*—Robert Davis
*Attorney, Agent, or Firm*—John C. Thompson; Alan S. Korman

[57] ABSTRACT

A polymerization apparatus includes a first chamber and a second chamber and a flexible, radioparent diaphragm separating the first chamber from the second chamber. A radiation source emitting polymerization-inducing radiation into the first chamber is provided. The second chamber is adapted for receiving a model and a foil, positioned between the diaphragm and the model, to be subjected to the radiation of the radiation source. A device for generating a pressure differential between the first and the second chamber for deflecting the diaphragm toward the model to thereby deform the foil at the model is provided. An adjusting device for adjusting the distance between the model and the diaphragm is provided.

16 Claims, 3 Drawing Sheets

POLYMERIZATION APPARATUS

BACKGROUND OF THE INVENTION

The present invention relates to a polymerization apparatus including a radiation source for emitting radiation for inducing polymerization, especially radiation in the form of light, into a first chamber, comprising a flexible radioparent membrane or diaphragm that separates the second chamber from a first chamber, whereby into the second chamber a model to be subjected to radiation is placed, especially a tooth stump, and whereby between the model and the membrane a foil is provided. The membrane, with the aid of a differential pressure, is deflected into the second chamber toward the model in order to deform the foil about the model.

Such a polymerization apparatus is known from International Patent Application WO 95/08300. In this polymerization apparatus a piece of pre-impregnated matrix material is placed onto a tooth stump or another model The term model in the context of the present invention refers to positive molds as well as negative molds.

Due to the differential pressure between the two chambers in the apparatus, a soft and flexible diaphragm positioned in the apparatus is forced onto the model (mold) so that the foil is pressed onto the model and is shaped according to the contour of the model.

A problem of such polymerization apparatus is ensuring a precise and reliable polymerization by light curing. Especially in the case of dental replacement parts, it is imperative that complete curing takes place whereby complete curing must be ensured within a limited amount of time. Thus, in general, output-intensive light sources (high luminous power) with corresponding spectra are used. For thermal as well as energetic reasons, the light electrical power usage should not be too great especially since high light intensity light sources are comparatively expensive to replace on a regular basis when spent.

In the apparatus known from the aforementioned application the light radiation must penetrate the flexible diaphragm and this results in certain losses of luminous power. Furthermore, the distance between the tooth stump and the light source must be selected such that for all model sizes occurring in practice sufficient space is provided. On the other hand, the luminous power is reduced more than proportionally with increasing distance so that measures for increasing luminous power have become known.

These measures include, for example, the teaching disclosed but not discussed in detail in the aforementioned publication. For improving the reflection of light beams within the area of the radiation source special reflectors in the form of an annular mirror 19 that fills the entire model chamber are provided.

The cycle times for the actual light curing process is determined substantially by how fast the required vacuum can be generated within the model chamber.

For the deformation of the foil which must adhere to the contour of the model, the application of a uniform high force is required which in practice is realized by a corresponding pressure differential. This pressure differential in connection with partly rugged or fissured models result in a considerable stress load of the flexible diaphragm. The diaphragm must therefore be exchanged quite frequently for safety reasons because a small hole or crack within the diaphragm would have disadvantageous results in regard to the molding process.

It is therefore an object of the present invention to provide a polymerization apparatus of the aforementioned kind with which the light output as well as the service life of the diaphragm can be improved.

SUMMARY OF THE INVENTION

A polymerization apparatus according to the present invention is primarily characterized by:

A first chamber and a second chamber;

A flexible, radioparent diaphragm separating the first chamber from the second chamber;

A radiation source emitting polymerization-inducing radiation into the first chamber;

The second chamber adapted for receiving a model and a foil, positioned between the diaphragm and the model, to be subjected to the radiation of the radiation source;

A device for generating a pressure differential between the first and the second chamber for deflecting the diaphragm toward the model to thereby deform the foil about the model;

An adjusting device for adjusting a distance between the model and the diaphragm.

The second chamber has a support device for the model, wherein a height of the support device and a distance to the diaphragm is adjustable.

The support device preferably comprises a support plate and an exchangeable support insert for supporting the support plate.

The support insert is a spacer ring.

The second chamber comprises pressure-stable filling bodies positioned external to the area in which the model and the foil are located and external to the area between the diaphragm and the foil.

The device for generating a pressure differential includes an air supply connected to the first chamber for introducing air to create the pressure differential in the form of a greater pressure in the first chamber than in the second chamber.

The device for generating a pressure differential includes a first vacuum source connected to the first chamber and a second vacuum source connected to the second chamber, the first and second vacuum sources adapted to produce a vacuum relative to the atmosphere surrounding the polymerization apparatus.

The first chamber comprises a cover and the radiation source is positioned above the cover of the first chamber, wherein the cover comprises a radioparent pane.

The polymerization apparatus further comprises an infrared filter positioned between the radiation source and the first chamber.

Preferably, the second chamber comprises a closure device for pressure-tightly closing the second chamber.

Advantageously, the polymerization apparatus comprises a first part and a second part detachably connected to one another, wherein the first part includes the first chamber and the diaphragm and the second part includes the second chamber.

The polymerization apparatus also includes a closure device, wherein the first part is a top part including the radiation source and the second part is a bottom part, wherein the first part and the second part are connected to one another by the closure device.

The closure device is preferably a bayonet closure.

Preferably, the support device comprises a pedestal extending upwardly into the second chamber and receiving at least one of the models centrally within the second chamber.

The radiation source includes a plurality of individual lights arranged adjacent to one another.

Advantageously, the individual lights are focused on an area in which the model is positioned.

Expediently, the individual lights are arranged at an obtuse angle to one another and have an optical axis intercepting one another in the area in which the model is positioned.

Surprisingly, with the inventive height adjustability a plurality of advantages can be achieved, The diaphragm must not be as deflectable as in the prior art so that its stress load is greatly reduced and its service life is greatly improved. The elimination of the annular mirror also allows in practice that the model with the foil can be brought closer to the diaphragm. Thus, the distance to the radiation source or light sources can be reduced so that the luminous power is improved. It is understood that, if desired, the entire interior of the polymerization apparatus can be provided with reflective surfaces.

The minimally required deflection of the diaphragm is also favorable in regard to light-technological considerations. It can be made of thin material with better light transmissivity without reducing its service life.

According to an advantageous embodiment it is suggested that filling bodies are positioned laterally to the pedestal of the model. The filling bodies are provided with reflective surfaces. With the inventive embodiment the time required for applying the pressure differential (to apply a greater pressure to the first chamber as compared to the second chamber) can be greatly reduced because a considerable number of filling bodies can be provided which are pressure-stable so that the model chamber thus has a reduced amount of air space that must be evacuated. This also results in a correspondingly reduced operating time and/or output requirement for the vacuum pump.

According to an especially advantageous embodiment, it is suggested to operate the apparatus with a single pump that removes air from the model chamber into the compression chamber i.e., guides air from the second chamber into the first chamber. This allows for an especially effective operation, and an additional vacuum pump can be eliminated.

According to a further preferred embodiment, it is suggested to provide the height adjustability by employing inserts. The adjusting device, for example, can be in the form of a spacer sleeve that is exchangeable and can be placed under the support plate for the models. The inserts can also be embodied as a filling body and can thus reduce the space to be evacuated.

According to another especially preferred embodiment, it is suggested to realize the adjusting device for the inventive height adjustment by providing snap-on positioning elements provided at the circumferential inner wall of the model chamber. They allow for a spring-loaded snapping of the support plate into the inner wall. The support plate is provided at its periphery with spring-loaded balls that are positioned at locations matching the locations within the inner walls so that after surpassing the snap-on force a movement of the support plate in the downward or upward direction is possible.

According to another advantageous embodiment, it is suggested that the inventive adjusting device comprises a support mechanism for the support plate that allows vertical displacement. With a pressure-tight force transmission device extending into the apparatus, the height adjustment can be actuated from the exterior so that a height adjustment can be performed even after closing the polymerization apparatus.

The pressure-tight force transmission device can, for example, be realized by an axle which penetrates the model chamber wall so that a pivot bearing for the height adjustment is possible. In order to maintain the support plate in a horizontal position this embodiment preferably includes a pantograph guiding mechanism (parallelogram guide) for the support plate.

According to a further preferred embodiment of the adjusting device, it is suggested that the adjusting device is operated with a drive motor, especially an electric motor, positioned within the model chamber. For example, small electric motors can be flanged to the bottom of the support plate which are provided with pinions that mesh with toothed racks positioned at the inner wall of the model chamber. It is understood that the thus formed gear system should be embodied so as not to require lubrication and should, for example, be comprised of plastic in order to prevent contamination of the foil to be polymerized in the vacuum in the chamber.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 4.

Figure 1:
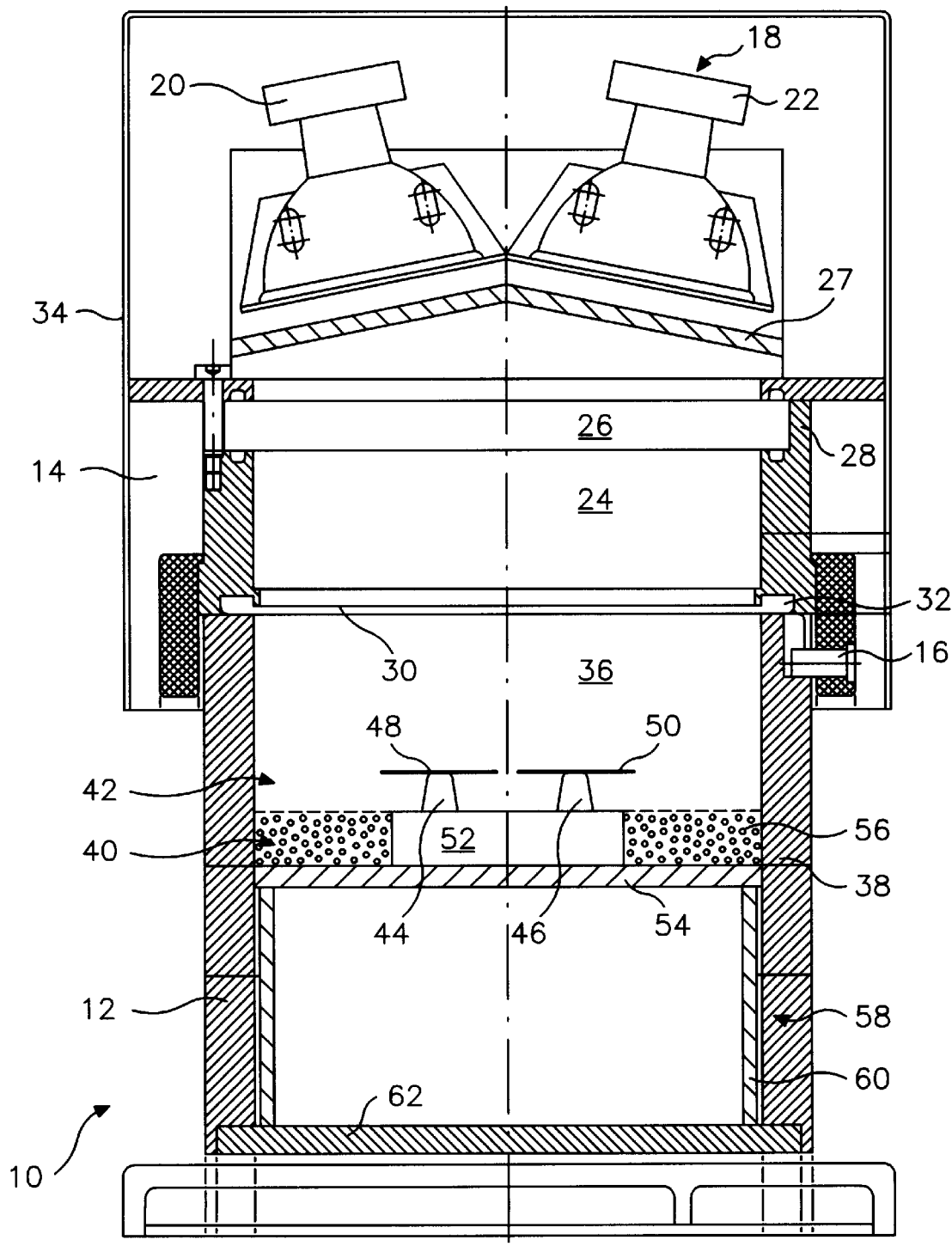
FIG. 1 is a first embodiment of the inventive polymerization apparatus.

The embodiment represented in FIG. 1 of a polymerization device 10 comprises a bottom part 12 and a top part 14. The top part 14 is detachably connected to the bottom part 12 for which purpose a bayonet closure 16 is provided. The top part 14 comprises a radiation source 18 with two lights 20 and 22 that emit radiation within the spectrum of visible light, optionally with a minimal UV light portion. It is understood that instead of the lights 20 and 22 other radiation devices suitable for light curing can be used. The lights 20 and 22 are arranged so as to be slightly slanted so that they focus on an area slightly below the end of the top part 14. They are cooled with a non-represented blower and are supported just above a first chamber (compression chamber) 24 of the top part 14. The compression chamber 24 comprises a cover 26 that is radioparent for the radiation emitted by the radiation source 18. An annular wall 28 extends in a circular fashion about the compression chamber 24. Between the radiation source 18 and the cover 26 an infrared filter 27 is provided in order to reduce the heat loading of the polymerization apparatus 10.

The compression chamber 24 is closed off in the downward direction by a diaphragm 30 that is flexible and expandable. It is clamped at its outer circumference with beads 32 in the annular wall 28. The top part 14 comprises furthermore a protective cover 34 which covers the entire height of the top part 14.

The annular wall 28 has a pressure connector (air supply), not represented in FIG. 1, with which the compression chamber 24 can be pressurized. For this purpose a non-represented compressor is provided.

The bottom part 12 comprises a second chamber (model chamber) 36 that is surrounded by pressure-tight model chamber walls 38. Within the model chamber 36 a support device 40 is provided that serves for supporting a model 42. The model 42 can include a number of tooth stumps 44, 46 whereby in the shown embodiment two toothed stumps are shown. A foil 48, 50 is positioned thereon. The support device 40 provides a pedestal 52 for the tooth stumps 44 and 46. The pedestal 52 is resting on a support plate 54 whereby the space between the model chamber wall 38 and the pedestal 52 is preferably filled with ball-shaped filling bodies 56. The filling bodies 56 serve to reduce the free air space within the model chamber 36 as well as to support the diaphragm 30 during the molding process. The support device 40, respectively, its pedestal may also be part of the model, or its height can be adjusted, for example, by placing spacer plates underneath.

The inventive adjusting device 58 comprises in the represented embodiment an exchangeable spacer ring 60 which is supported on the bottom 62 of the bottom part 12. Its height determines the level of the support plate 54 and thus the distance between the foil 48 and the diaphragm 30. It is inventively suggested, depending on the size of the tooth stumps, respectively, of the model, to employ spacer rings 60 of different heights so that the model is always positioned as close as possible to the diaphragm 30.

The filling bodies 56 are preferably provided with a reflective surface so that the polymerization-inducing radiation is reflected thereat and can reach the foils 48, 50. The inner surfaces of the annular wall 28 and of the model chamber 36 are also preferably reflective which also increases the light output or luminous power.

The model chamber 36 is provided with a non-represented vacuum connector that is connected to a vacuum source (vacuum pump) also not shown in the drawing. The vacuum connector allows to evacuate the model chamber 36 and provides for a deep drawing of the foils 48 and 50.

The deep drawing and polymerization process is carried out as follows.

In a first step, while the apparatus is open, a suitable spacer ring for the model to be treated is selected. It is inserted and the support plate 54 is placed onto the spacer ring. The model 42 is then centrally arranged on the support plate 54 and the surrounding area is filled with reflective plastic balls 56 such that the filling is approximately flush with the upper side of the pedestal 52.

Subsequently, foils 48, 50 are placed onto the tooth stumps 44, 46. The foils are comprised of a light-polymerizable plastic material having imbedded therein fiberglass. With the aid of the bayonet closure 16 the top part 14 and the bottom part 12 are connected to one another so that the polymerization apparatus 10 forms a pressure-tight unit. The first chamber 24 as well as the second chamber 36 are supplied with vacuum whereby the top part 14 and the bottom part 12 are forced onto one another. The beads 32 that serve as an annular seal are simultaneously compressed and the bayonet closure 16 can be snapped into place.

Subsequently, the vacuum in the first chamber 24 is replaced with pressure of approximately 2 bar. At this point the lights 20, 22 can be switched on with low output in order to be able to monitor visually the model 42 through a view port in the wall. The pressure of 2 bar within the compression chamber 24 forces the highly flexible and radioparent diaphragm 30 onto the foils 48 and 50. The foils 48, 50 are thus pressed onto the respective tooth stump 40 and 46 in order to be molded thereto. In this state the output of the radiation source 18 is increased to maximum output and the polymerization or light curing of the foil is carried out while full pressure is present within the compression chamber 24.

After completion of polymerization, the pressure is released from the compression chamber 24 and the compression chamber 24 is maintained at normal pressure (atmospheric pressure) or is optionally under slight vacuum. In this state the bayonet closure can be opened, and the vacuum within the model chamber 36 is released.

Figure 2:
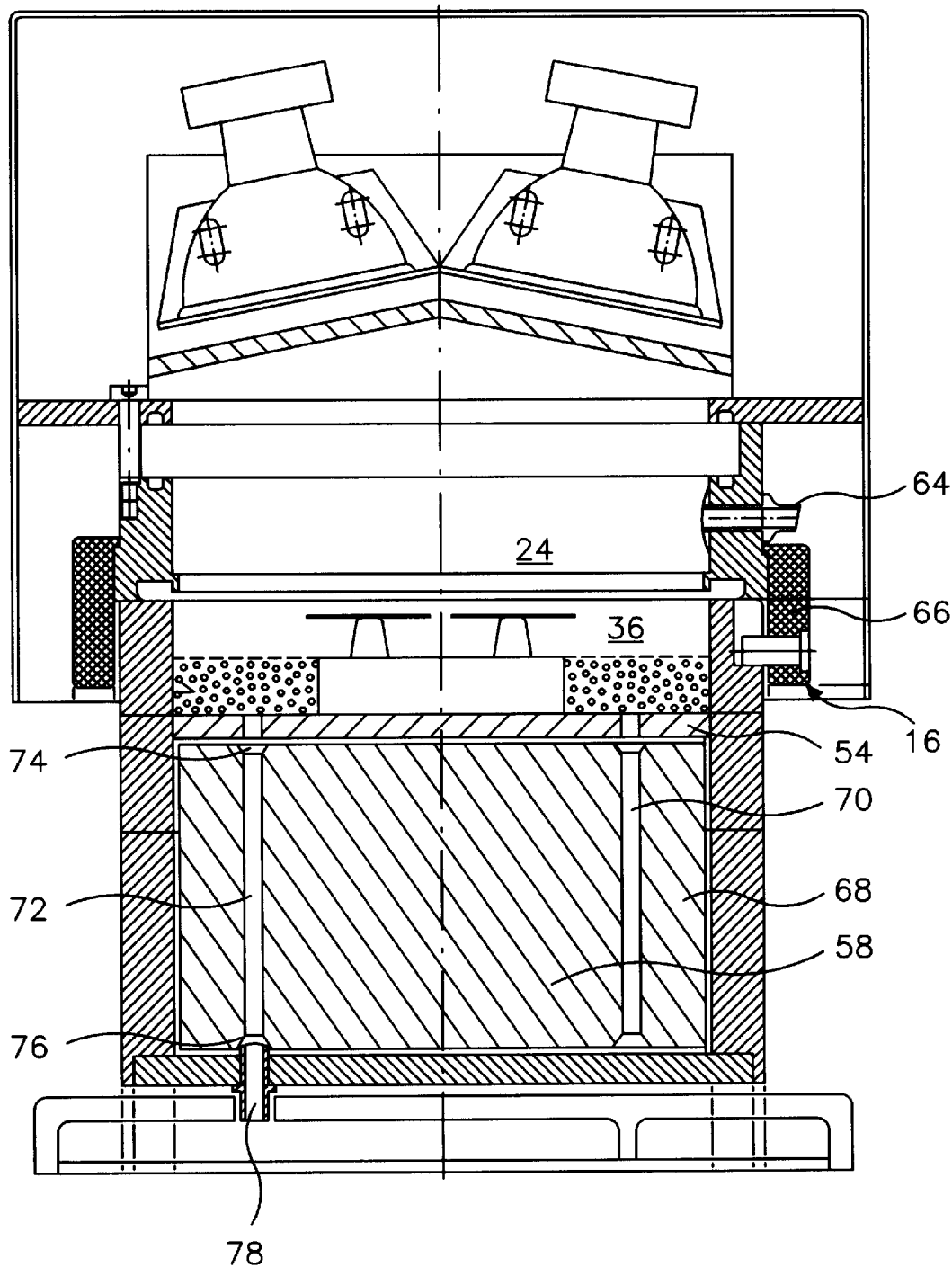
FIG. 2 is a second embodiment of the inventive polymerization apparatus.

A modified embodiment of the inventive polymerization device 10 can be seen in FIG. 2. This apparatus is more compact than the polymerization apparatus according to FIG. 1. It can be supplied faster with pressure or vacuum and with less energy expenditure. The height of the compression chamber 24 is reduced to about half in comparison to FIG. 1. In order to connect the air supply 64, a securing ring 66 of the bayonet closure 16 is embodied somewhat lower at the location of air supply connection 64. Furthermore, the model chamber is reduced to the possible minimum size and the model 42 extends to a position in close vicinity below the diaphragm 30. The diaphragm 30 in this embodiment thus must be flexible only to a minimal extend in comparison to the embodiment according to FIG. 1. This is beneficial in regard to increasing its service life.

Instead of the spacer ring 60 a spacer body 68 is positioned below the support plate 54. The spacer body 68 fills the entire space below the support plate 54.

The spacer body 68 comprises vacuum channels 70, 72 which extend over its entire height. The vacuum channels 70, 72 open into annular channels 74, 76 which extend annularly about the distance body 68 at its upper side, respectively, underside. With corresponding bores in the support plate 54 the introduction of vacuum via a vacuum source 78 into the upper area of the model chamber 36 is possible.

The air supply connector 64 as well as the vacuum source connector 78 are connected to non-represented pump which, with respective switching valves, can provide vacuum to the first and second chamber as well as pressure to the first chamber.

Figure 3:
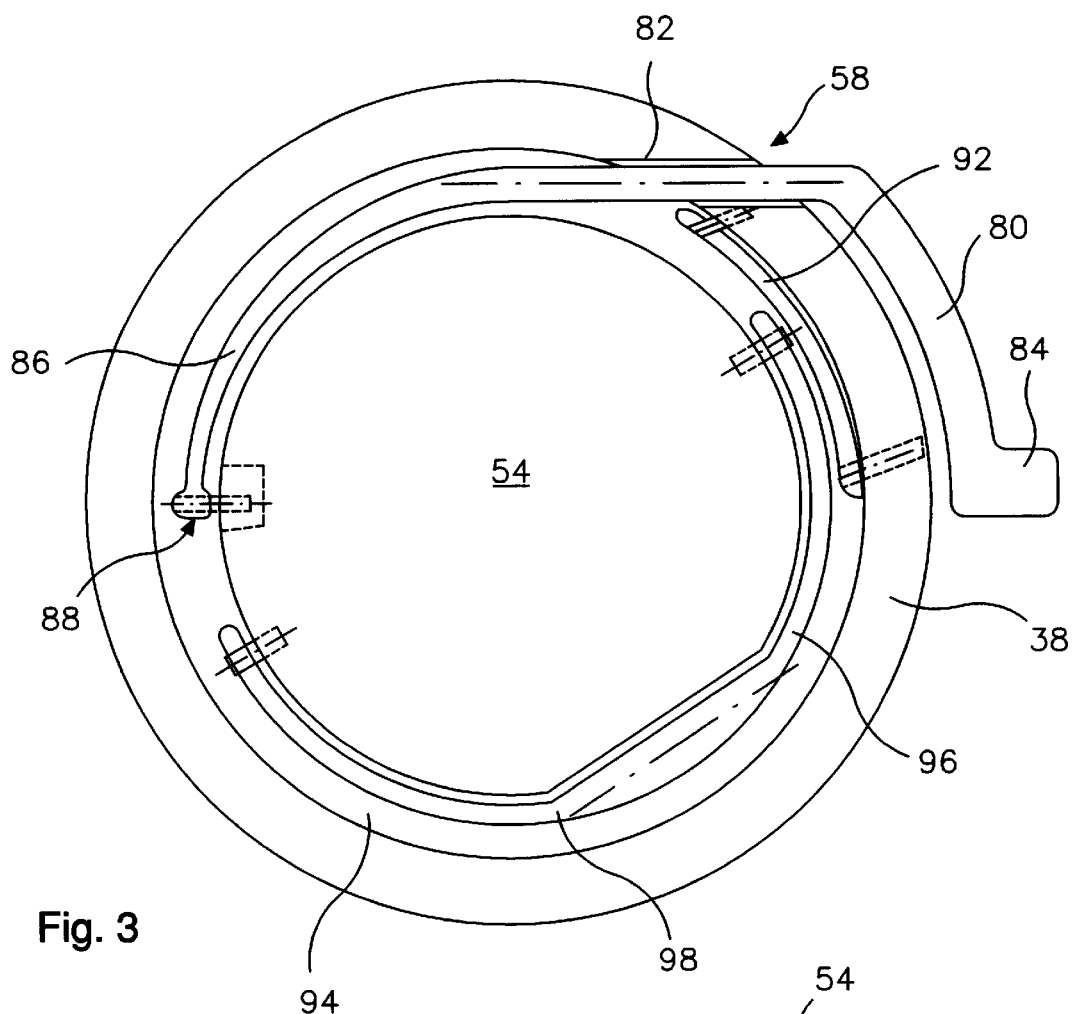
FIG. 3 is a plan view of the bottom part with removed top part of a further embodiment of the inventive polymerization apparatus.
Figure 4:
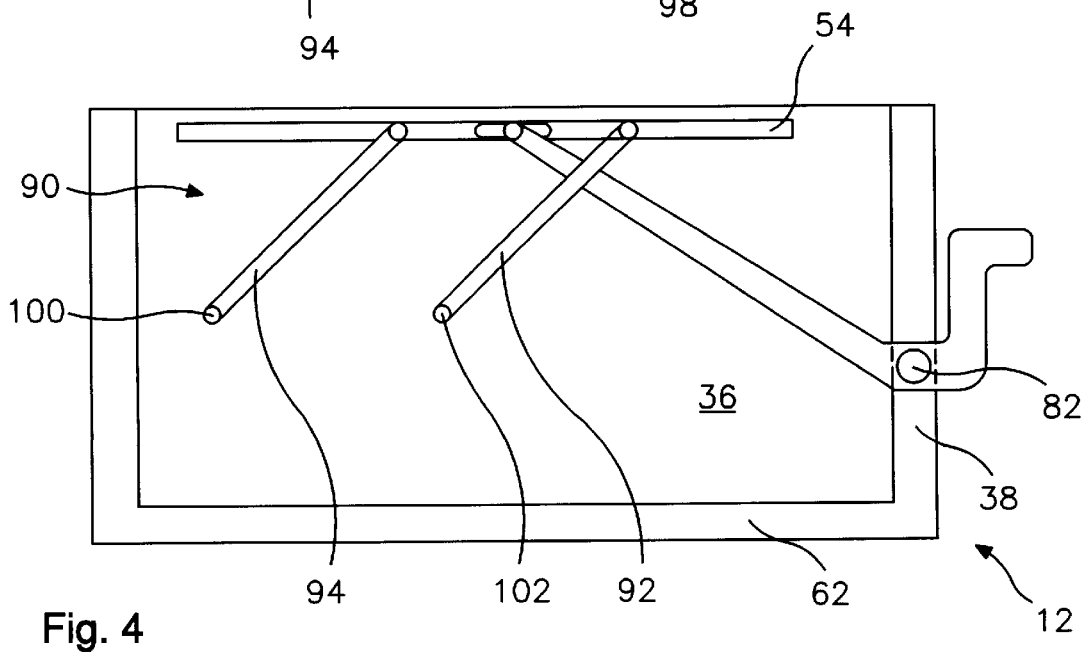
FIG. 4 is a schematic side view of the embodiment of FIG. 3.

A modified embodiment of the adjusting device 58 is shown in FIGS. 3 and 4. In this embodiment the adjusting device 58 includes a lever 80 which is supported in a bearing bushing 82 at the model chamber wall 38. The lever 80 comprises a grip 84 with which the position of the support plate 54 can be adjusted from the exterior of the apparatus. The lever 80 penetrates the model chamber wall 38 approximately tangentially to the support plate 54 and extends as a curved portion 86 following the model chamber wall 38. It is of a small height in the horizontal direction. The lever 80 comprises at the end of the curved portion 86 a pivot joint 88 for the support plate 54. The pivot axis of the pivot joint 88 extends parallel to the axis of the bearing bushing 82.

The support plate 54 can be height-adjusted with this adjusting device 58. However, it is also desirable that it maintains its horizontal orientation. For this purpose, the parallelogram guiding mechanism (pantograph) 90 shown in FIG. 4 is provided which comprises two guide rods 94. As can be seen in FIG. 4, the guide rods 92 and 94 which in their projection onto their pivot axis extend parallel to one another have the same length. However, they are curved in order to extend exterior to the support plate 54. The guide rod 92, as can be seen in FIG. 3, guides the support plate 54 only at one side while the guide rod 94 comprises two legs 96, 98 which surround the support plate 94 in a curved fashion. The lever 80 is supported in a slotted hole of the support plate for compensating the pivot movement of the parallelogram guiding mechanism, as is shown in FIG. 4.

The bearing locations 100 and 102 of the guide rods 94, 92, viewed in the vertical direction, are positioned approximately at the same level and approximately at the level of the center of the model chamber 36. The bearing bushing 82 is also arranged at this level. With this embodiment it is possible to transfer the support plate 54 from the position shown in FIG. 4 into the lowermost position in which it is adjacent to the bottom 62 of the bottom part 12.

This embodiment allows for a fast height adjustment with the inventive adjusting device, but requires that the model chamber 36 is substantially free of filling bodies.

According to a further embodiment, it is suggested to embody the bottom 62 of the bottom part 12 as a pressure-tight piston that can be displaced by actuation from the exterior. The bottom 62 thus provides an adjusting device and it is possible to actuate this adjusting device 58, 62 from the exterior while ensuring a minimum free air space within the model chamber 36.

In a further alternative of this embodiment, the bottom 62 is fixedly connected to the support surface and the entire polymerization apparatus, exclusive of the bottom and the model placed thereon, is height-adjustable. The inventive adjusting device can also be realized by this embodiment.

The present invention is, of course, in no way restricted to the specific disclosure of the specification and drawings, but also encompasses any modifications within the scope of the appended claims.

What is claim is:

1. A polymerization apparatus comprising:
    a first chamber and a second chamber;
    a flexible, radioparent diaphragm separating said first chamber from said second chamber;
    a radiation source emitting polymerization-inducing radiation into said first chamber;
        said second chamber adapted for receiving a model and a foil, positioned between said diaphragm and the model, to be subjected to the radiation of said radiation source;
    a device for generating a pressure differential between said first and said second chamber for deflecting said diaphragm toward the model to thereby deform the foil about the model;
    an adjusting device for adjusting a distance between the model and said diaphragm; and pressure-stable filling bodies positioned approximately laterally of the model to reduce deflection of the diaphragm as the foil is being deformed about the model.

2. A polymerization apparatus according to claim 1, wherein said second chamber has a support device for the model, wherein a height of said support device and a distance to said diaphragm is adjustable.

3. A polymerization apparatus according to claim 2, wherein said support device comprises a support plate and an exchangeable support insert for supporting said support plate.

4. A polymerization apparatus according to claim 3, wherein said support insert is a spacer ring.

5. A polymerization apparatus according to claim 1, wherein said device for generating a pressure differential includes an air supply connected to said first chamber for introducing air to create said pressure differential in the form of a greater pressure in said first chamber than in said second chamber.

6. A polymerization apparatus according to claim 1, wherein said device for generating a pressure differential includes a first vacuum source connected to said first chamber and a second vacuum source connected to said second chamber, said first and second vacuum sources adapted to produce a vacuum relative to an atmosphere surrounding said polymerization apparatus.

7. A polymerization apparatus according to claim 1, wherein said first chamber comprises a cover and wherein said radiation source is positioned above said cover of said first chamber, wherein said cover comprises a radioparent pane.

8. A polymerization apparatus according to claim 1, further comprising an infrared filter positioned between said radiation source and said first chamber.

9. A polymerization apparatus according to claim 1, wherein said second chamber comprises a closure device for pressure-tightly closing said second chamber.

10. A polymerization apparatus according to claim 1, comprised of a first part and a second part detachably connected to one another, wherein said first part includes said first chamber and said diaphragm and said second part includes said second chamber.

11. A polymerization apparatus according to claim 10, further comprising a closure device, wherein said first part is a top part including said radiation source, and wherein said second part is a bottom part, wherein said first part and said second part are connected to one another by said closure device.

12. A polymerization apparatus according to claim 11, wherein said closure device is a bayonet closure.

13. A polymerization apparatus according to claim 2, wherein said support device comprises a pedestal extending upwardly into said second chamber and receiving at least one of the models centrally within said second chamber.

14. A polymerization chamber according to claim 1, wherein said radiation source includes a plurality of individual lights arranged adjacent to one another.

15. A polymerization chamber according to claim 14, wherein said individual lights are focussed on an area in which the model is positioned.

16. A polymerization chamber according to claim 14, wherein said individual lights are arranged at an obtuse angle to one another and have an optical axis intercepting one another in the area in which the model is positioned.

* * * * *